United States Patent
Festag et al.

(10) Patent No.: US 7,518,368 B2
(45) Date of Patent: Apr. 14, 2009

(54) DEVICE AND METHOD FOR OPTICAL TRANSMISSION OF MAGNETIC RESONANCE SIGNALS IN MAGNETIC RESONANCE SYSTEMS

(75) Inventors: Mario Festag, Berlin (DE); Martin Hergt, Châtelaine (CH); Markus Vester, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/014,189

(22) Filed: Jan. 15, 2008

(65) Prior Publication Data

US 2008/0169816 A1    Jul. 17, 2008

(30) Foreign Application Priority Data

Jan. 15, 2007    (DE) ....................... 10 2007 002 187

(51) Int. Cl.
G01V 3/00    (2006.01)
(52) U.S. Cl. ....................... 324/318; 324/322
(58) Field of Classification Search ......... 324/300–322; 128/716, 653, 696, 709, 378, 95; 455/602, 455/612; 250/551

See application file for complete search history.

(56) References Cited

U.S. PATENT DOCUMENTS

| | | | | |
|---|---|---|---|---|
| 4,763,075 A | * | 8/1988 | Weigert | ....................... 324/318 |
| 5,296,813 A | | 3/1994 | Holmes et al. | |
| 5,473,722 A | * | 12/1995 | Sohler et al. | ................. 385/132 |
| 5,572,130 A | * | 11/1996 | Ratzel | ......................... 324/318 |
| 5,644,416 A | * | 7/1997 | Morikawa et al. | ............. 349/86 |
| 7,233,148 B2 | | 6/2007 | Hergt et al. | |
| 2008/0164879 A1 | * | 7/2008 | Bollenbeck | ................. 324/322 |
| 2008/0238424 A1 | * | 10/2008 | Possanzini | .................. 324/318 |

FOREIGN PATENT DOCUMENTS

WO    WO 2006/008665    1/2006

OTHER PUBLICATIONS

"Optical MR Receive Coil Array Interconnect," Koste et al., Proc. Intl. Soc. Mag. Reson. Med., vol. 13 (2005), p. 411.

* cited by examiner

Primary Examiner—Brij B Shrivastav
(74) Attorney, Agent, or Firm—Schiff Hardin LLP

(57) ABSTRACT

In a transmission device for use in magnetic resonance systems for transmitting magnetic resonance signals from a number of local coils to an evaluation device, the signals are transmitted as optical signals in an optical conductor between a first transmitter-side transducer that transduces electrical signals into optical signals and a second receiver-side transducer that transduces optical signals into electrical signals, and an analog/digital converter is respectively provided between the local coils and the first, transmitter-side transducer. The local coils are connected by electronic elements to a single circuit board, and a number of preamplifiers, the analog/digital converters and a multiplexer are integrated onto the circuit board such that the multiplexer merges the outputs of the multiple analog/digital converters.

5 Claims, 1 Drawing Sheet

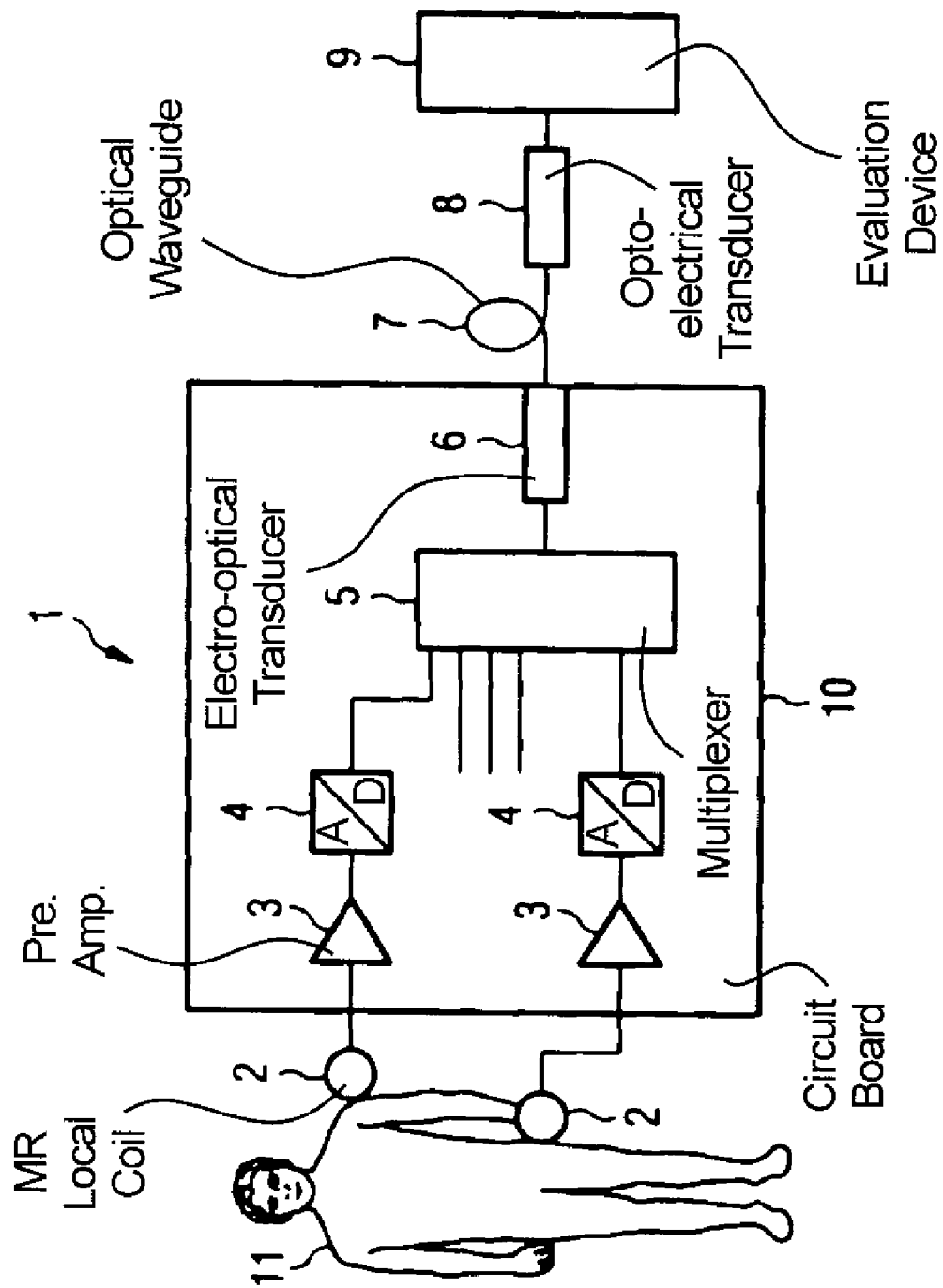

DEVICE AND METHOD FOR OPTICAL TRANSMISSION OF MAGNETIC RESONANCE SIGNALS IN MAGNETIC RESONANCE SYSTEMS

BACKGROUND OF THE INVENTION

1. Field of the Invention

The present invention concerns a device and a method for transmission of magnetic resonance signals from a number of local coils to an evaluation device, of the type wherein the signals are transferred as optical signals in an optical conductor between a first, transmitter-side transducer that transduces electrical signals into optical signals and a second, receiver-side transducer that transduces the optical signals into electrical signals, an optical conductor that conducts the optical signals, and wherein an analog/digital converter is provided between the local coils and the first, transmitter-side transducer.

2. Description of the Prior Art

Standard electrical conductors (for the most part coaxial cables) are used in conventional magnetic resonance systems in order to feed the magnetic resonance signals acquired by the local coils attached on the body of a patient to an evaluation device. Due to the radio-frequency alternating magnetic field predominating in the examination volume, currents known as sheath waves or common mode currents that exhibit the same frequency as the alternating magnetic field are induced in the electrical conductors. Without further measures, the common mode currents also flow into the human body due to the capacitive coupling with the patient. This must be avoided since internal burns can occur due to a current flow into the human body. This problem was previously solved by the components known as sheath wave barriers that are attached to the electrical conductors between the local coils and the evaluation device. A sheath wave barrier is formed by a parallel resonance circuit with a specific inductance L and a specific capacitance C connected in parallel. L and C must be tuned such that resonance occurs in the oscillating circuit at the frequency of the alternating magnetic field (and thus the frequency of the current induced in the electrical conductors). In the case of resonance in which the total resistance of the oscillating circuit is very high, the oscillating circuit (which inductively couples to the electrical conductor) maximally attenuates the current induced in the electrical conductor, which is why a sheath current no longer occurs on the electrical conductor and the human body (which is capacitively coupled with the electrical conductor); the sheath waves are thus suppressed. Since a number of such sheath wave barriers are required for the multiple electrical feed lines (one cable is required per local coil), the device is relatively complex, occupies a large volume and is costly. This known device is described in DE 102004015856 A1, for example.

Another approach to solve the problem of the currents induced in the electrical conductors by the alternating magnetic field is described by G. P. Koste, M. C. Nielsen, T. R. Tolliver, R. L. Frey, R. D. Watkins, GE Global Research Center, "Optical MR Receive Coil Array Interconnect", Proceedings ISMRM 2005, p. 411. The signal transmission in electrical conductors is replaced by optical signal transmission in optical fibers. Analog optical signals are transferred between the measurement unit (essentially formed by local coil and amplifier) and the evaluation unit that comprises a receiver that transduces the optical signals back into electrical signals. In the measurement unit, the transduction of electrical signals into optical signals occurs in a modulator (for example a Mach-Zehnder optical modulator made from $LiNbO_3$) into which laser light and electrical measurement signals are fed. The information from the signals of the local coils is thereby modulated to the laser light by intensity modulation. The modulated light is then analogously transferred to the receiver. Furthermore, it is important that $LiNbO_3$ is suitable for use in high magnetic fields. A disadvantage of such analog optical signal transfer with a modulator is that the signal/noise ratio is relatively poor, which is why the dynamic range (thus the capability of the system to differentiate between large and small signals) is limited. $LiNbO_3$ modulators are additionally relatively expensive.

Yet a further approach is to digitize the analog electrical signals of the local coils before the transfer to the evaluation device and to transduce the digital electrical signals into digital optical signals. This method is disclosed WO 2006/008665 A1. The signal/noise ratio is optimized by the early digitizing of the signals; influences by the strong magnetic fields are eliminated by the transfer as optical signals. A suitable electronic device with a transducer for transduction of electrical signals into optical signals is provided for each local coil.

As noted above, the solution with sheath wave barriers on the electrical conductors is thus that this is technically complicated and expensive.

Although the solution of analog optical transfer in connection with optical modulators avoids the problem of the sheath waves, the achievable signal/noise ratio is not satisfactory and the financial expenditure is relatively high.

A problem with the solution with digital optical transmission as described in WO 2006/008665 A1 is that a separate readout electronic each one electro-optical transducer must be provided for each local coil, which entails a relatively large space requirement and is costly.

SUMMARY OF THE INVENTION

An object of the present invention is to provide a signal transmission method in magnetic resonance systems in which no sheath waves occur, that exhibits an optimal signal/noise ratio, and that can be realized in an optimally small space with minimal costs.

The above object is achieved in accordance with the present invention by a transmission device of the type described above wherein the multiple local coils are connected via electronic elements to a single circuit board, on which a number of preamplifiers, the multiple analog/digital converters, and a multiplexer are integrated. The multiplexer multiplexes the respective outputs of the multiple analog/digital converters, and supplies an output signal to the transmitter-side transducer.

The present invention is advantageous for a number of reasons. The electronic components of the measurement device on a circuit board are so highly integrated (and thus concentrated in such a small space) that the inductance and capacitance are so low that the current induced by the radio-frequency alternating magnetic field in the circuit board (and thus also the parasitic capacitive coupling with the patient) is negligibly small. Particularly when a number of local coils relay their signals to a single electro-optical transducer, the use of a multiplexer leads to a minimal space requirement and minimal costs.

BRIEF DESCRIPTION OF THE DRAWING

The single FIGURE is a schematic illustration of an embodiment of a device for transmission of digital optical signals in magnetic resonance systems in accordance with the invention.

DESCRIPTION OF THE PREFERRED EMBODIMENTS

The FIGURE shows a transmission device 1 for use in magnetic resonance systems for transmitting magnetic resonance signals from a number of local coils 2 into an evaluation device 9. The signals are transmitted as optical signals in an optical conductor 7 between a first transmitter-side transducer 6 that transduces electrical signals into optical signals and a second receiver-side transducer that transduces optical signals into electrical signals. An analog/digital converter 4 is respectively provided between each of the local coils 2 and the first, transmitter-side transducer 6. The local coils 2 are connected via electronic elements to a single circuit board 10, and a number of preamplifiers 3, the analog/digital converters 4 and a multiplexer 5 are integrated onto the circuit board 10 such that the multiplexer 5 merges the outputs of many analog/digital converters.

In the exemplary embodiment shown in the FIGURE, a number of local coils 2 are connected via electronic elements to a single circuit board 10, and the preamplifiers 3, the analog/digital converters 4 and the multiplexer 5 are integrated onto the circuit board 10 and the one transmitter-side transducer 6 is likewise placed on the circuit board.

In another exemplary embodiment (not shown) a number of local coils 2 are connected via electronic elements to a single circuit board, and the preamplifiers 3, the analog/digital converters 4 and the multiplexer 5 are integrated onto the circuit board 10 and the output of the multiplexer 5 is connected to the input of a single, separate transmitter-side transducer 6.

The aforementioned electronic elements can be placed on a single, small circuit board measuring only a few cm$^2$.

The receiver-side transducer 8 with the downstream evaluation device 9 can be placed at a great distance from the measurement arrangement with transmitter-side transducer 6.

The invention furthermore concerns a method for transfer of magnetic resonance signals in magnetic resonance systems between a number of local coils 2 and an evaluation device 9, wherein the signals are optically transmitted between a first transmitter-side transducer 6 that transduces electrical signals into optical signals and a second receiver-side transducer that transduces optical signals into electrical signals, and wherein the analog electrical measurement signals are digitized before entering into the first transmitter-side transducer 6 and wherein the signals between the analog/digital converters and the first, transmitter-side transducer 6 are supplied to a multiplexer 5 and enter into the transmitter-side transducer 6 as multiplexed signals.

In the exemplary embodiments described above it is important that the electronic elements that are attached on a circuit board are so highly integrated that the currents induced in the circuit board by the alternating magnetic field are negligible. The danger of generating a current flow in the body of the patient 11 by capacitive coupling with the patient 11 in the magnetic resonance measurement, which current flow can lead to internal burns, is thereby prevented. Furthermore, it is advantageous to replace the coaxial cable, as used in the prior art (in which sheath wave barriers must neutralize the induced currents), with an optical transmission medium that is naturally not influenced by magnetic fields. Furthermore, it is a particular advantage of the invention that the signal/noise ratio is optimized by only the internal noise due to the sampling of the digitizing occurring as noise due to the early analog/digital conversion. In all following elements that the digitized signal passes through, no further noise is added. The dynamic range (thus the capability of the system to differentiate between large and small signals) is optimized by the early digitizing. In addition to the protection of the patient from induced currents, the most important feature of the claimed invention is that, by the aforementioned high integration of the electronic elements in connection with a multiplexer that is likewise mounted on the circuit board, the electrical signals of a number of local coils are all supplied to the multiplexer and the resulting electrical signal is transferred to the transmitter-side transducer where it is converted into an optical signal.

Although modifications and changes may be suggested by those skilled in the art, it is the intention of the inventors to embody within the patent warranted hereon all changes and modifications as reasonably and properly come within the scope of their contribution to the art.

We claim as our invention:

1. A transmission device for use in a magnetic resonance system having a plurality of local coils, for transmitting magnetic resonance signals from the local coils to an evaluation device, said transmission device comprising:

a single circuit board;

a plurality of preamplifiers integrated on the circuit board, said preamplifiers respectively having inputs configured to receive magnetic resonance signals from the local coils;

a plurality of analog/digital converters integrated on the circuit board respectively having inputs connected to outputs of the preamplifiers;

a multiplexer integrated on said circuit board having a plurality of inputs respectively connected to outputs of said analog-digital converters, said multiplexer multiplexing the outputs of the analog/digital converters at a single multiplexer output;

an electro-optical transducer having an input connected to the output of the multiplexer, said electro-optical transducer transducing the output of the multiplexer into an optical signal;

an optical waveguide connected to an output of the electro-optical transducer that transmits the optical signal to a location remote from the electro-optical transducer and the circuit board; and an opto-electrical transducer connected to the waveguide that converts the optical signal from the waveguide into an electrical output signal, said opto-electrical transducer having an output at which the electrical signal is present configured for connection to the evaluation unit.

2. A transmission device as claimed in claim 1 wherein said electro-optical transducer is also integrated on said circuit board.

3. A transmission device as claimed in claim 1 wherein said electro-optical transducer is located separate from said circuit board.

4. A transmission device as claimed in claim 1 wherein said circuit board has a size comprising a few cm$^2$.

5. A method for transferring magnetic resonance signals in a magnetic resonance system between a plurality of local coils and evaluation device, comprising the steps of:

detecting magnetic resonance signals with a plurality of local coils, each coil emitting an analog coil output signal;

in a plurality of analog/digital converters, respectively converting the analog coil output signals into respective digital signals;

multiplexing said plurality of digital signals to produce a single multiplexed digital output signal;

transducing said multiplexed digital output signal into an optical signal;

transmitting the optical signal to a remote reception location; and at the remote reception location, transducing the optical signal into an electrical reception signal.

\* \* \* \* \*